United States Patent [19]

Creuzet et al.

[11] Patent Number: 4,590,193
[45] Date of Patent: May 20, 1986

[54] 3-(2-(4-PHENYLPIPERAZINYLETHYL) ANILINO)-ISOBENZOFURANONES, THEIR METHOD OF PREPARATION AND THEIR USE AS ANTIHYPERTENSIVE AND ANTIALLERGIC DRUGS

[75] Inventors: Marie-Hélène Creuzet, Bordeaux; Claude Feniou, Pessac; Francoise Guichard, Bordeaux; Gisèle Prat, Talence; Henri Pontagnier, Pessac, all of France

[73] Assignee: Societe Cortial, S.A., Paris, France

[21] Appl. No.: 517,653

[22] Filed: Jul. 27, 1983

[30] Foreign Application Priority Data

Jul. 29, 1982 [FR] France .................. 82 13446

[51] Int. Cl.$^4$ .................. A61K 31/495; C07D 241/04
[52] U.S. Cl. .................. 514/253; 544/376; 544/377; 544/392
[58] Field of Search .................. 544/376; 424/250; 514/253

[56] References Cited

PUBLICATIONS

Creuzet, et al., "Chemical Abstracts", vol. 101, 1984, col. 101:2331pc.

Primary Examiner—Glennon H. Hollrah
Assistant Examiner—James H. Turnipseed
Attorney, Agent, or Firm—Oblon, Fisher, Spivak, McClelland & Maier

[57] ABSTRACT

This invention relates to 3-(2-(4-phenylpiperazinylethyl)anilino)-isobenzofuranones, their method of preparation and their use in the treatment of conditions such as hypertension, and allergies.

These compounds are characterized by the formula:

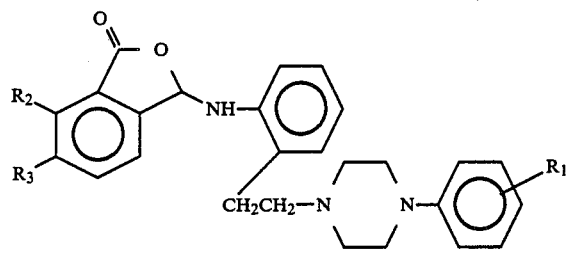

in which $R_1$ may be one or more substituents located at the ortho, meta, or para positions selected from the group of H, $CH_3$, $CF_3$, F, Cl and $OCH_3$; $R_2$ and $R_3$ are the same or different and are H or $OCH_3$. These compounds are in the form of free bases or their pharmaceutically safe salts. They can be obtained by a reaction between a 2-(phenylpiperazinylethyl) aniline and an aromatic aldehyde having an acid function at the ortho position of the carboxaldehyde function.

These derivatives are useful for the treatment of hypertension and allergic conditions.

17 Claims, No Drawings

3-(2-(4-PHENYLPIPERAZINYLETHYL)ANILINO)-ISOBENZOFURANONES, THEIR METHOD OF PREPARATION AND THEIR USE AS ANTIHYPERTENSIVE AND ANTIALLERGIC DRUGS

BACKGROUND OF THE INVENTION

1. Field of the Invention

The present invention relates to antihypertensive and antiallergic compounds, and more particularly to isobenzofuranones, to a method of preparing these compounds, and to their use in the treatment of hypertension and allergic conditions.

2. Description of the Prior Art

Amine compounds are already known in the prior art. These include compounds having the general structrure:

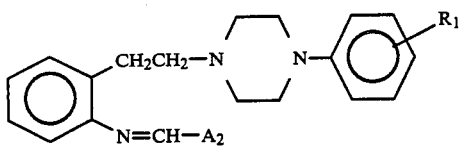

which have been described in French Pat. No. 81 20563 of Nov. 3, 1981. These compounds however, due to presence of a —CH=N— imine bond in their structure, are significantly unstable in an acidic medium. A need, therefore, continues to exist for compounds having improved stability, useful for the treatment of hypertension and allergic conditions.

SUMMARY OF THE INVENTION

It is, therefore, an object of the present invention to provide antihypertensive and antiallergic compounds.

Another object of the invention is to provide antihypertensive and antiallergic compounds having improved stability in an acidic medium.

It is another object of the present invention to provide phamacological compositions comprising antiallergic and antihypertensive compounds.

Still another object of the invention is to provide a method of decreasing hypertension and treating allergic conditions in animals, including humans.

Further another object of this invention is to provide a method of synthesizing the antihypertensive and antiallergic compounds.

These and other objects of the invention, as will hereinafter become more readily apparent, have been attained by providing:

A 3-(2-(4-phenylpiperazinylethyl)anilino)isobenzofuranone of the formula:

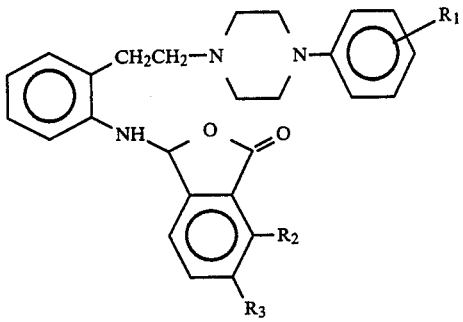

wherein:
$R_1$ may be one or more substituents located at the ortho, meta or para position and represents a radical selected from the group consisting of H, $CH_3$, $CF_3$, F, Cl and $OCH_3$;
$R_2$ and $R_3$ may be the same or different, and represent H or $OCH_3$. These products can be in the form of the free bases, or their pharmaceutically safe salts, such as hydrochloride, citrates or benzilates.

The objects of the invention have also been attained by providing pharmacological compositions comprising the aforementioned isobenzofuranones, methods of obtaining the isobenzofuranones, and methods of treating hypertension and allergic conditions in animals, including humans, comprising using the present isobenzofuranone compounds.

BRIEF DESCRIPTION OF THE PREFERRED EMBODIMENTS

The compounds of the present invention comprise those having the formula:

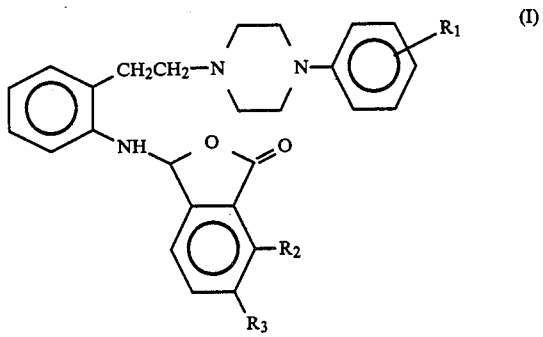

In this formula, $R_1$ may be one or more substituents, located in the ortho, meta, or para positions and are selected from the group consisting of H, $CH_3$, $CF_3$, F, Cl and $OCH_3$. $R_2$ and $R_3$ are the same or different and are selected from the group consisting of H and $OCH_3$. The isobenzofuranones of this invention may be in the form of free bases or acid addition salts thereof. Common acid addition salts are hydrochloric acid salts, citric acid salts and benzilic acid salts.

The isobenzofuranone compounds of formula (I) can be synthesized by a condensation reaction between an amine of general formula:

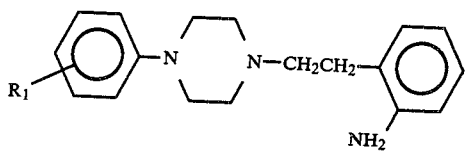

and an aromatic aldehyde of general formula:

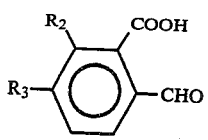

having an acid function at the ortho position at the carboxaldehyde function. The amine compounds of formula (II) are fully described in the French Pat. No. 81 20564 of Nov. 3, 1981. The text of French Pat. No. 81 20564, except the claims and the title, is reproduced below.

The invention relates to novel 2-(4-phenylpiperazinyl-ethyl)anilines, the method of preparing them, and their use in therapy.

These products have the general formula:

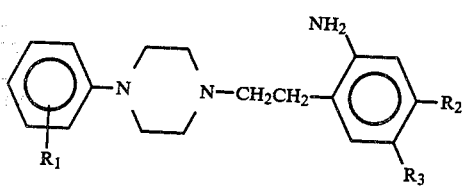

where $R_1$ is hydrogen or one or more ortho, meta, or para substituents such as $CH_3$, $CF_3$, F, Cl, OR or $OCH_3$; and $R_2$ and $R_3$ (which are identical or different) are H, a lower alkoxy group with 1 to 4 C atoms, or together $R_2$ and $R_3$ comprise a chain $—O—(CH_2)_n—O—$ with $n=1$ or 2, or a chain $—O—CH_2—O—CH_2—$.

These products may be employed in the form of the free base or in the form of their pharmaceutically suitable salts (such as hydrochlorides, citrates, or benzilates).

Derivatives of 3-(4-phenylpiperazinylethyl)aniline or 4-(4-phenylpiperazinylethyl)aniline are known such as those described in Special Medical Patent Nos. 191M and 208M. Also derivatives of 2-piperazinylaniline are known which have a methyl group substituted on the nitrogen in the 4-position of the piperazine (French Patent Application No. 80-03774). We have recently discovered that, whereas the derivatives described in French Patent Application No. 80-03774 have psychotropic activity of the anxiolytic or antidepressant type, derivatives having formula (I) supra have antihistaminic and antiallergenic activity, which enables them to be used therepeutically, particularly in allergology.

The known synthetic antihistamines of therapeutic value belong primarily to the following chemical families: phenothiazine (promethazine), cycloheptane (cyproheptadine), ethylenediamine (antazoline), aminoethanol (doxylamine), propylamine (tripolidine), and diphenylmethylpiperazine (cinnarizine). The inventive products thus do not belong to any of the families of antihistamines which are presently therapeutically employed.

The products having formula (I) are prepared in general by a reaction of a 2-(2-halogenoethyl)nitrobenzene and an N-phenylpiperazine, with subsequent reduction of the nitro derivative thus obtained.

The invention will be described in more detail with the aid of the following Examples:

EXAMPLE 1

Preparation of 2-(4-phenylpiperazinylethyl)aniline

A mixture comprising 0.1 mol 2-(2-bromoethyl)nitrobenzene, 0.23 mol N-phenylpiperazine, and 300 cc absolute ethanol was heated for 15 hr with agitation and refluxing of the ethanol. The alcohol was then removed by evaporation. The residue of the evaporation was dissolved in water. This was then extracted with ether. The ether phase was washed with fresh water, and then dried over sodium sulfate, after which the ether was evaporated off. The excess N-phenylpiperazine was removed by distillation. The distillation residue was recrystallized in methanol, yielding 2-(4-phenylpiperazinylethyl)nitrobenzene with m.p.=76° C.

This nitro derivative was dissolved in methanol, and 7–8 g Raney nickel was added to the solution. The mixture was held under hydrogen, with agitation, until the reaction was completed. The Raney nickel was removed by filtration, and the solvent by evaporation.

The 2-(4-phenylpiperazinylethyl)aniline was isolated by crystallization of the evaporation residue dissolved in a mixture of ethyl ether and petroleum ether. Melting point was 103° C.

EXAMPLE 2

The following derivatives of formula (I) were prepared by the method described in Example 1:

$R_1$=4-fluoro-: m.p. 113° C.
$R_1$=3-trifluoromethyl-: m.p. 64° C.
$R_1$=3-methoxy-: m.p. 103° C.
$R_1$=4-chloro-: m.p. 126° C.
$R_1$=2-methyl-: m.p. 97° C.

EXAMPLE 3

Preparation of 4,5-methylenedioxy-2-[4-(3-trifluoromethylphenyl)-piperazinylethyl]aniline A mixture of 22.9 g of 6-(2-chloroethyl)-5-nitro-1,3-benzodioxole, 69 g of N-(3-trifluoromethylphenyl)piperazine, and 150 cc of ethanol was heated at 120° C. for 18 hr, under agitation. The ethanol was then removed by evaporation. The residue was dissolved in a mixture of ether and water. The ether phase was separated by decantation and extracted with a 2N aqueous HCl solution. The hydrochloride of 5-nitro-6-[4-(3-trifluoromethylphenyl)piperazinylethyl]-1,3-benzodioxole partially precipitated. The precipitate was filtered out and reunited with the aqueous acid phase; this mixture was alkalized, then extracted with fresh ether, and dried over sodium sulfate. The ether was eliminated by evaporation, and the residue was recrystallized from fresh water. Melting point 91° C.

27 g of the nitro derivative thus prepared was suspended in 1.5 liter methanol, 7–8 g Raney nickel was added, and the mixture was held under hydrogen until the reaction was completed. The Raney nickel was removed by filtration, and the filtrate was evaporated. The evaporation residue was recrystallized from a mixture of ethyl ether and petroleum ether, to yield 4,5-methylenedioxy-2-[4-(3-trifluoromethylphenyl)- piperazinylethyl]aniline, which was purified by recrystallization from methanol. Melting point 88° C.

There follows a Table of the principal RMN spectral characteristics of the products prepared according to Examples 1-3, in CDCl$_3$ solution. The chemical displacements with respect to TMS taken as an internal standard are given, along with the number of protons and the multiplicity of the peaks. Peak descriptions are coded as follows: mc=broad and complex; s=singlet; d=dome-shaped.

| R$_1$ | R$_2$, R$_3$ | —CH$_2$— | NH$_2$ | Aromatic protons | Miscellaneous |
|---|---|---|---|---|---|
| H | H, H | 2.5-3.3 ppm;12H;mc | 3.9 ppm;2H;d | 6.4-7.4 ppm;9H;mc | |
| CH$_3$—2 | H, H | 2.4-3.2 ppm;12H;mc | 3.9 ppm;2H;d | 6.4-7.3 ppm;8H;mc | 2.2 ppm;3H;s CH$_3$—C |
| *Cl—4 | H, H | 2.5-3.4 ppm;12H;mc | 4.2 ppm;2H;d | 6.5-7.4 ppm;8H;mc | |
| OCH$_3$—2 | H, H | 2.5-3.3 ppm;12H;mc | 4.0 ppm;2H;d | 6.5-7.2 ppm;8H;mc | 3.8 ppm;3H;s CH$_3$—O |
| F—4 | H, H | 2.5-3.3 ppm;12H;mc | 3.9 ppm;2H;d | 6.5-7.2 ppm;8H;mc | |
| CF$_3$—3 | —O—CH$_2$—O— | 2.4-3.4 ppm;12H;mc (CH$_2$CH$_2$—N) 5.8 ppm;2H;s (—O—CH$_2$—O—) | 3.7 ppm;2H;d | 6.2 and 6.5 ppm;2H;s (H of the aniline ring) 6.9-7.5 ppm;4H;mc (H of the phenyl-piperazine rings) | |

*Solvent: CDCl$_3$ + 3 drops of DMSO(d$_6$)

The products of the present invention were subjected to various pharmacological tests; selected results of these are given infra.

The lethal dose of the inventive products was determined using Swiss mice free of specific pathogenic organisms. The LD$_{50}$ (in 14 days of observation) of the product of Example 1 administered as a 20 wt. % "Tween" solution was 1175 mg/kg (range of lethal doses: 946–1459).

The antihistaminic activity was determined in vitro by measuring the concentration which caused 50% inhibition of histamine-induced contractions on isolated guinea pig ileum (histamine strength $10^{-8}$ g/liter). The CI$_{50}$ of the product of Example 1 was, after rinsing away the histamine applied, $6.3 \times 10^{-6}$ g/ml (range: 4.14–9.58).

The antiallergic activity was determined in the following test of passive cutaneous anaphylaxis: Male Sprague-Dawley rats were administered intradermally 0.1 ml serum rich in IgE. This serum was produced by sensitizing Sprague-Dawley rats with an i.p. injection of ovalbumin and a suspension of Bordetella pertussis, followed 30 days thereafter by a second injection of ovalbumin. 24 Hrs. after the administration of the serum, 0.5 ml of a solution containing 8.25 mg/kg ovalbumin and 26.4 mg/kg Evans blue in a buffer at pH 7.05 was administered intravenously. After 30 min, the animals were sacrificed. Each papule was excised, and incubated at 37° C. in 15 g formamide for 4 days. The quantity of Evans blue contained in each papule was determined by measuring the optical density of the mixture. The product to be tested was administered p.o. in a homogeneous suspension in "Tween 80", 10 min before the allergenic injection. The activity of said product was measured as the percent dimunution of the quantity of Evans blue which diffused into the papule. For the product of Example 1, the DE$_{50}$ was 5.11 mg/kg (range: 3.39–7.76).

In view of their antihistaminic and anaphylactic activity, coupled with their low toxicity, the inventive products are therapeutically useful, alone or in combination, in the treatment of allergic and anaphylactic conditions such as urticaria, pruritises, dermatoses, eczemas, hay fever, Quincke's edema, serum sickness, asthma, and anaphylactic shock. They also may be employed for preventive or curative purpose in the treatment of motion sickness.

They can be administered orally, e.g. in the form of dragees, compresses tablets, syrups, or capsules; rectally e.g., in the form of suppositories; intramuscularly or intravenously; or topically e.g. in the form of an ointment or gel. The dosage employed will vary, according to the indication and the patient: from 2–200 gm/da in 2 to 6 doses orally, from 2–200 mg/da in 1 or 2 doses rectally, or from 0.5–50 mg by parenteral injection.

The 3-(2-(4-phenylpiperazinylethyl)anilino)isobenzofuranones of the present invention exhibit antianaphylactic, antihistaminic, antiseritononergic and antihypertensive properties, and thus, are useful in the treatment of cardiovascular and allergic conditions.

In view of the their antihistaminic, antiserotoninergic and antianaphylactic properties combined with their extremely low toxicities' the products of this invention are useful used alone, or in association with other drugs, in the treatment of allergic and anaphylactic states, such as urticaria, pruritus, dermatosis, eczema, hay fever, Quincke's edema, serum sickness, asthma and anaphylactic shock. They can also be used for the prevention or treatment of motion sickness. In addition, the antihypertensive properties of these compounds make them useful alone or in association with a diuretic, and/or other antihypertensive medications in the treatment of arterial hypertension.

The modes and manner of administration of the present compound are several. The present compounds, can be administered for example orally in the form of sugar-coated pills, tablets, syrups or ampules. These compounds can also be administered rectally, in the form of suppositories. In addition, the present compounds can also be administered intramuscularly or intravenously, as well as topically in the form of ointments or gels.

The present isobenzofuranone compounds are placed in a known pharmaceutically acceptable vehicle, the nature of which varies depending on the mode of administration of the present compounds. The isobenzofuranones of the present invention can be provided to animals, including domestic animals and humans, suffering from hypertension or allergic conditions.

The dosage and mode of administration will depend on the seriousness of the condition, the age, sex and physical condition of the patient, concurrent administration of other drugs, counterindications and the like. Generally, a dosage of between one to 100 mg per day for a normal adult would be sufficient when administered orally or rectally. Orally, these drugs can be administered in two to six doses per day while rectally, they can administered in one or two doses per day. When injected parentally, the doses is from 0.5 to 50 mg per day.

Having now generally described this invention, the same will be understood by reference to certain specific pharmacological tests, which the present isobenzofuranone compounds have been subjected to. The results of some of these tests are shown below.

PHARMACOLOGICAL TESTS
TOXICITY STUDIES

The mortality induced by these substances was determined by using Swiss mice which were free of specific pathogenic organisms. The animals were kept in an air conditioned room for 24 to 48 hours prior to the beginning of the experiments. The substances were solubilized in Tween and administered either intragastrically or intraperitoneally.

The results shown in Tables I and II are expressed in percentage of mortality as a function of the dose administered, or by the dose inducing 50% mortality ($LD_{50}$) determined by the Bliss method.

TABLE I

| | ORAL TOXICITY | | | |
|---|---|---|---|---|
| | Doses in mg/kg | | | |
| PRODUCT | 750 | 1000 | 2000 | 3000 |
| COR34 30 | | 0 | 0 | 10 |
| COR34 37 | 0 | 10 | 50 | |
| COR34 41 | 0 | 10 | 10 | |
| COR34 42 | | 0 | 0 | |
| COR34 43 | | 0 | 0 | |
| COR34 47 | | 0 | 0 | |
| COR34 48 | | 0 | 0 | |
| COR34 49 | | 0 | 0 | |
| COR34 53 | | 0 | 20 | |

TABLE II

| | INTRAPERITONEAL TOXICITY | | | | | | | | $LD_{50}$ |
|---|---|---|---|---|---|---|---|---|---|
| | Dosage in mg/kg | | | | | | | | |
| PRODUCT | 100 | 200 | 300 | 400 | 500 | 800 | 900 | 1000 | in mg/kg |
| COR34 30 | 0 | 10 | 0 | | 0 | | | | |
| COR34 37 | | | | | 20 | | 60 | | |
| COR34 41 | | | | 0 | 25 | 35 | 50 | 70 | 873 (700–1091) |
| COR34 43 | | | | | 0 | 0 | | 0 | |
| COR34 47 | | | | | 0 | | | 0 | |
| COR34 48 | | | | | 0 | | | 0 | |
| COR34 49 | | | | | 0 | | 20 | | |
| COR34 53 | | | | | 60 | | | 100 | 500 (429–582) |

BIOLOGICAL ACTIVITY STUDIES

The antihistamine activity was determined in vitro by measuring the concentration causing a 50% inhibition of the contractions induced by a solution of histamine ($10^{-8}$ g/l) on a guinea pig ileum ($IC_{50}$). The antagonist is administered at the same time as the agonist or before. In the latter case, the time of contact between the antagonist and the organ isolated before the introduction of the agonist is shown in Table III. The results of these experiments are shown in Table III.

TABLE III

| | IN VITRO ANTIHISTAMINE ACTIVITY | |
|---|---|---|
| PRODUCT | $IC_{50}$ in M/l | Time of Contact |
| COR34 30 | $1.04 \times 10^{-6}(4.91 \times 10^{-7} - 2.20 \times 10^{-6})$ | |
| COR34 37 | $1.55 \times 10^{-8}(1.11 \times 10^{-8} - 2.17 \times 10^{-8})$ | 3 mm |
| COR34 41 | $3.11 \times 10^{-8}(2.55 \times 10^{-8} - 3.86 \times 10^{-8})$ | 10 mm |
| COR34 42 | $3.3 \times 10^{-8}(2.7 \times 10^{-8} - 4.01 \times 10^{-8})$ | 5 mm |
| COR34 43 | $3.53 \times 10^{-6}(2.76 \times 10^{-6} - 4.54 \times 10^{-6})$ | |
| COR34 47 | $2.9 \times 10^{-8}(1.9 \times 10^{-8} - 4.6 \times 10^{-8})$ | 3 mm |
| COR34 48 | $5.5 \times 10^{-8}(3.34 \times 10^{-8} - 9.04 \times 10^{-8})$ | 5 mm |
| COR34 49 | $8.10^{-8}(6.3 \times 10^{-8} - 1 \times 10^{-7})$ | 10 mm |
| COR34 53 | about $1.5 \times 10^{-6}$ | 5 mm |
| Promethazine | $4.93 \times 10^{-9}(3.10 \times 10^{-9} - 7.83 \times 10^{-9})$ | 15 mm |
| Chlorpromazine | $3.63 \times 10^{-6}(2.18 \times 10^{-6} - 4.20 \times 10^{-6})$ | |

The products of this invention are competitive antagonists of histamine. Of these compounds, COR 34 30 exhibits a $pA_2$ of 7.69, COR 34 37 a $pA_2$ of 7.86, COR 34 41 a $pA_2$ of 8.03 and COR 34 43 a $pA_2$ of 7.97. Table IV shows the antiserotonin activity of the present products. This activity is expressed as the concentration of in vitro compound which inhibits 50% of the contractions induced by serotonin ($5.10^{-7}$ g/ml) on an isolated guinea pig ileum ($IC_{50}$).

TABLE IV

| | ANTISEROTONIN ACTIVITY | |
|---|---|---|
| PRODUCT | $IC_{50}$ in M/l | Time of Contact |
| COR34 30 | $9.33 \times 10^{-6}(5.39 \times 10^{-6} - 1.62 \times 10^{-5})$ | 5 mm |
| COR34 37 | $2.27 \times 10^{-5}(2.16 \times 10^{-5} - 2.39 \times 10^{-5})$ | 5 mm |
| COR34 41 | $1.26 \times 10^{-5}(9.45 \times 10^{-6} - 1.70 \times 10^{-5})$ | 15 mm |
| COR34 43 | $2.05 \times 10^{-5}(1.45 \times 10^{-5} - 2.90 \times 10^{-5})$ | 3 mm |
| COR34 47 | $1.97 \times 10^{-5}(1.66 \times 10^{-5} - 2.38 \times 10^{-5})$ | 3 mm |
| COR34 48 | $6.46 \times 10^{-6}(5.04 \times 10^{-6} - 8.31 \times 10^{-6})$ | 5 mm |
| Promethazine | $4.44 \times 10^{-7}(2.69 \times 10^{-7} - 7.32 \times 10^{-7})$ | 3 mm |
| Cyproheptadine | $1.41 \times 10^{-7}(8.56 \times 10^{-8} - 2.34 \times 10^{-7})$ | 3 mm |

The in vivo antihistamine activity is determined in the awake guinea pig by testing the bronchospasm induced by a 0.3% histamine aerosol. The antihistaminic activity of the present products is tested upon their oral administration in Tween. The percentages of animals protected at the end of 1 h and 6 h with a dosage of 10 mg/kg are given in Table V.

TABLE V

| | IN VIVO ANTIHISTAMINE ACTIVITY | |
|---|---|---|
| | % of animals protected at | |
| PRODUCT | 1 h | 6 h |
| COR34 30 | 60 | 40 |
| COR34 37 | 70 | 70 |
| COR34 41 | 90 | 60 |
| COR34 43 | 90 | 50 |
| COR34 47 | 20 | 0 |
| COR34 48 | 40 | 10 |
| COR34 49 | 30 | 20 |

The antiallergic activity has been determined in Sprague Dawley rats by the test for cutaneous passive anaphylaxis. Anaphylaxis is induced by the intradermal administration of a serum rich in IgE, followed 24 hours later by the intravenous injection of a solution containing ovalbumin and Evans blue. The activity of the products to be tested, administered per os, is estimated as the percentage of reduction in the amount of Evans blue having diffused at the injection point. Table VI provides the ED50 expressed in mg/kg of certain products of this invention.

The products of this invention were administered orally to rats in the model of the cutaneous reactions. These reactions were induced by intradermal administration of histamine, serotonin, or the 48/80 compound. The activity of these products is expressed as the percentage of reduction in the amount of blue dye having diffused at the injection point, and the obtained values for ED50 expressed in mg/kg are given in Table VI.

TABLE VI

| | ANTIALLERGIC ACTIVITY | | | |
|---|---|---|---|---|
| | Cutaneous passive | CUTANEOUS REACTIONS INDUCED BY | | |
| PRODUCT | Anaphylaxis | Histamine | Serotonin | 48/80 |
| COR34 30 | 3.8(2.5–5.7) | 12.1(8.5–17) | 13.2(8.7–19.9) | 11.2(7.9–15.9) |
| COR34 37 | 6.4(4.9–8.5) | 9.3(6.6–13.2) | 7.9(6.0–10.5) | 9.4(7.1–12.3) |
| COR34 41 | 4.1(2.3–7.1) | 7.9(5.3–12.0) | 14.0(8.7–22.9) | 10.9(6.3–19.0) |
| COR34 42 | 14.8(9.1–24) | | | |
| COR34 43 | 6.6(4.1–10.7) | 9.1(4.9–17) | 17.1(13.8–20.9) | 11.1(7.2–16.6) |

The products of this invention exhibit antihypertensive activity. Some examples of compounds showing this activity are given below.

In the spontaneously hypertensive awake rat the compound COR 34 41 causes a drop in AP of 18.8% at 25 mg/kg per os, and it causes a drop in AP of 19.3% at 50 mg/kg. The AP returns to normal at the end of an hour, at a dosage of 25 mg/kg, and at the end of 5 hours with a dosage of 50 mg/kg.

The compound COR 34 42 causes a AP drop of 15.6% at a dose of 50 mg/kg per os. The AP returns to normal at the end of 5 hours.

When administered orally to spontaneously hypertensive rats at a rate of 50 mg/kg every 12 hours for five days, COR 34 41 causes a drop in the AP. The AP becomes stable at the end of the treatment, at a value of about 18 mm Hg below its initial value. The effect on motility when giving the present substances orally to mice, was tested by using an actimeter. The ED50 as a sedative for COR 34 30 is about 50 mg/kg, for COR 34 42 is 10 mg/kg, for COR 34 49 it is 18 mg/kg and for COR 34 48 it is 9 mg/kg.

In order to further illustrate the present invention the following examples on the synthesis of the present compounds are presented. The specific conditions and proportions in these examples are presented as being typical only, and should not be construed to limit the scope of the present invention unduly.

EXAMPLES

EXAMPLE 1

Synthesis of the 3-(2-(4-phenylpiperazinylethyl)anilino)-isobenzofuranone (a product of formula I with $R_1=R_2=R_3=H$; (code name COR 34 30)

A mixture consisting of 0.025 mole of 3-(2-(4-phenyl-piperazinylethyl)aniline, 0.023 mole of phthalaldehydic acid and 300 to 400 cc of benzene is heated with reflux while stirring. The water is eliminated as it is formed using a Dean and Stark trap. When the reaction is completed, the benzene is evaporated and the evaporation residue is crystallized in a mixture of ethyl ether and petroleum ether. The solid residue is filtered and recrystallized in ethanol.

The product of Example 1 is obtained by this procedure with a yield of 77%. This product has the following characteristics:

Melting point: 180° C.
Molecular mass: 413.5.
Microanalysis: Calculated: C: 75.52, H: 6.57, N: 10.16, O: 7.74. Found: C: 75.76, H: 6.66, N: 10.03, O: 7.54.
NMR in CDCl$_3$: 2.3–3.0 ppm, 12 protons, complex massif (CH$_2$); 6.4–7.7 ppm, 15 protons, complex massif (aromatic protons+

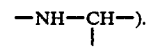

EXAMPLE 2

Synthesis of the 3-(2-(4-methoxyphenylpiperazinylethyl)anilino)isobenzofuranone (a product of formula I with $R_1=OCH_3$-4, $R_2=R_3=H$; code name COR 34 53)

This product is prepared according to the same method described in Example 1 from 2-(4-paramethoxy-phenylpiperazinylethyl)-aniline and phthalaldehydic acid with a yield of 62%. This product has the following characteristics:

Molecular mass: 443.5.
Microanalysis: Calculated: C: 73.11, H: 6.59, N: 9.47, O: 10.82. Found: C: 72.53, H: 6.61, N: 9.42, O: 11.51.
NMR in CDCl$_3$: 2.1–3.0 ppm, 12 protons, complex massif (CH$_2$); 3.7 ppm, 3 protons, singlet (OCH$_3$); 6.4–7.8 ppm, 14 protons, complex massif (aromatic protons+

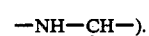

EXAMPLE 3

Synthesis of the 3-(2-(4-fluorophenylpiperazinylethyl)anilino)isobenzofuranone (a product of formula I with $R_1=F$-4, $R_2=R_3=H$; code name COR 34 37)

This product is prepared according to the same method described in Example 1 from 2-(p-fluorophenyl-piperazinylethyl)-aniline and phthalaldehydic acid with a yield of 84%. This product has the following characteristics:

Molecular mass: 431.5.
Melting point: 184° C.

Microanalysis: Calculated: C: 72.37, H: 6.06, N: 9.74, F: 4.40. Found: C: 72.09, H: 6.35, N; 9.51, F: 4.41.

NMR in CDCl$_3$: 2.2–3.0 ppm, 12 protons, complex massif (CH$_2$); 6.4–7.8 ppm, 14 protons, complex massif (aromatic protons+

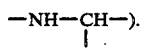

EXAMPLE 4

Synthesis of the 3-(2-(4-(2-methoxyphenylpiperazinylethyl)anilino)-)isobenzofuranone (a product of formula I with R$_1$=OCH$_3$-2, R$_2$=R$_3$=H; code name COR 34 41)

This product is prepared as described in Example 1 from 2-(4-(2-methoxyphenyl)piperazinylethyl)aniline and phthalaldehydic acid with a yield of 82%. This product has the following characteristics:

Molecular mass: 443.5.
Melting point: 173° C.
Microanalysis: Calculated: C: 73.11, H: 6.59, N: 9.47, O: 10.82. Found: C: 72.75, H: 6.58, N: 9.42, O: 10.59.

MNR in CDCl$_3$: 2.2–3.1 ppm, 12 protons, complex massif (CH$_2$); 3.7 ppm, 3 protons, singlet (CH$_3$O); 6.3–8.0 ppm, 14 protons, complex massif (aromatic protons+

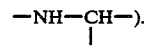

EXAMPLE 5

Synthesis of the 3-(2-(4-(2-methylphenyl)piperazinylethyl)-aniline)isobenzofuranone (a product of formula I with R$_1$=CH$_3$-2, R$_2$=R$_3$=H; code name COR 34 49)

This product is prepared according to the same method described in Example 1 from 2-(4-(2-methylphenyl)piperazinylethyl)aniline and phthalaldehydic acid with a yield of 67%. This compound has the following characteristics:

Molecular mass: 427.6.
Melting point: 174° C.
Microanalysis: Calculated: C: 75.85, H: 6.84, N: 9.83, O: 7.48. Found: C: 75.61, H: 6.76, N: 9.91, O: 7.49.

NMR in CDCl$_3$: 2.0–3.0 ppm, 15 protons, complex massif (CH$_2$+CH$_3$); 6.3–8.0 ppm, 14 protons, complex massif (aromatic protons+

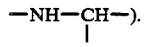

EXAMPLE 6

Synthesis of the 6,7-dimethoxy-3-(2-(4-phenylpiperazinylethyl-)anilino)isobenzofuranone (a product of formula I with R$_1$=H, R$_2$=R$_3$=CH$_3$O; code name COR 34 47)

This product is also prepared according to the method of Example 1 from 2-(4-phenylpiperazinyle-thyl)aniline and opianic acid with a yield of 78%. The characteristics of the compound are as follows:

Molecular mass: 473.6.

Melting point: 199° C.
Microanalysis: Calculated: C: 71.01, H: 6.60, N: 8.87, O: 13.51. Found: C: 70.59, H: 6.60, N: 8.75, O: 13.84.

NMR in DMSOD$_6$: 2.4–3.3 ppm, 12 protons, complex massif (CH$_2$); 3.6 and 3.8 ppm, 6 protons, singlets (2 OCH$_3$); 6.6–8.1 ppm, 13 protons, complex massif (aromatic protons+

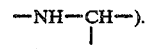

EXAMPLE 7

Synthesis of the 6,7-dimethoxy-3-(2-(4-p-fluorophenylpiperazinylethyl)-anilino)isobenzofuranone (a product of formula I with R$_1$=F-4, R$_2$=R$_3$=OCH$_3$; code name COR 34 43)

This product is also prepared according to the method of Example 1 from 2-(4-p-fluorophenyl-piperazinylethyl)-aniline and opianic acid with a yield of 82%. The compound of this example shows the following characteristics:

Molecular mass: 493.5.
Melting point: 210° C.
Microanalysis: Calculated: C: 68.42, H: 6.15, N: 8.54, F: 3.86. Found: C: 68.44, H: 6.08, N: 8.48, F: 3.77.

NMR in the DMSOD$_6$: 2.4–3.1 ppm, 12 protons, complex massif (CH$_2$); 3.6 and 3.8 ppm, 6 protons, singlets (2 OCH$_3$); 6.5–7.7 ppm, 12 protons, complex massif (aromatic protons+

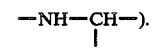

EXAMPLE 8

Synthesis of the 3-(2-(4-p-chlorophenylpiperazinylethyl)-aniline)-6,7-dimethoxyisobenzofuranone (a product of formula I with R$_1$=Cl-4, R$_2$=R$_3$=OCH$_3$; code name COR 34 42)

This product is prepared according to the method described in Example 1 from 2-(4-p-chlorophenyl-piperazinylethyl)-aniline and opianic acid with a yield of 58%. The characteristics displayed by the present compound are as follows:

Molecuar mass: 508.0.
Melting point: 199° C.
Microanalysis: Calculated: C: 66.20, H: 5.95, N: 8.27, O: 12.60, Cl: 6.98. Found: C: 66.08, H: 5.98, N: 7.83, O: 13.27, Cl: 6.79.

NMR in the DMSOD$_6$: 2.4–3.1 ppm, 12 protons, complex massif (CH$_2$); 3.6 and 3.8 ppm, 6 protons, singlets (2 OCH$_3$); 5.6 ppm, 1 proton, dome (NH); 6.6–7.5 ppm, 11 protons, complex massif (aromatic proton+

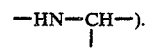

EXAMPLE 9

Synthesis of the 6,7-dimethoxy-3-(2-(4-(2-methylphenylpiperarzinylethyl)anilino)-isobenzofuranone (a product of formula I with $R_1=(CH_3-2)$, $R_2=R_3=OCH_3$, code name COR 34 48)

This product is also prepared according to the method described in Example 1 from 2-(4-(2-methylphenyl)piperazinylethyl)aniline and opianic acid with a yield of 88%. The following are the characteristics displayed by the present compound:

Molecular mass: 487.6.
Melting point: 180° C.
Microanalysis: Calculated: C: 71.43, H: 6.82, N: 8.62, O: 13.12. Found: C: 71.42, H: 6.86, N: 8.69, O: 13.27.

NMR in $DMSOD_6$: 2.2 ppm, 3 protons, singlet ($CH_3$-C); 2.4–3.2 ppm, 12 protons, complex massif ($CH_2$); 3.7–3.8 ppm, 6 protons, singlet (2 $OCH_3$); 6.6–8.1 ppm, 12 protons, complex massif (aromatic protons +

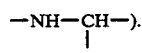

Having now fully described the invention, it will be apparent to one of ordinary skill in the art that many changes and modifications can be made thereto, without departing from the spirit of the invention as set forth herein.

What is claimed as new and desired to be secured by Letters Patent of the United States is:

1. The compound of the formula

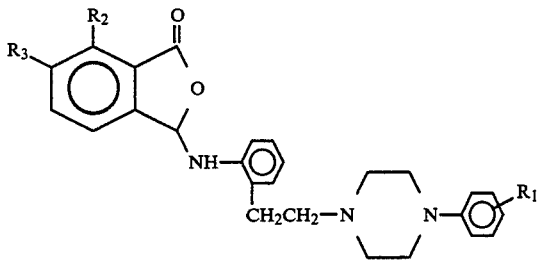

wherein:

$R_1$, may be one or more substituents located at the ortho, meta or para positions, and represents a radical selected from the group consisting of H, $CH_3$, $CF_3$, F, Cl and $OCH_3$; and $R_2$ and $R_3$, may be the same or different, and represent H or $OCH_3$; or pharmaceutically acceptable addition salts thereof.

2. The compound of claim 1 wherein the addition salt is selected from the group consisting of hydrochloric acid salt, citric acid salt and benzilic acid salt.

3. The compound of claim 1, wherein $R_1$ is a single substituent.

4. The compound of claim 3 wherein $R_1$ is H or $OCH_3$.

5. A pharmaceutical composition useful for treating a condition selected from the group consisting of allergies, hypertension, uriticaria, pruritus, dermatosis, eczema, hay fever, Quincke's edema, serum sickness, asthma and anaphylactic shock, comprising:

an effective amount of one of the compounds of claim 1, or a combination thereof; and a pharmaceutically safe excipient.

6. The pharmaceutical composition of claim 5 wherein the excipient is suitable for the oral administration of said composition.

7. The pharmaceutical composition of claim 6 wherein the composition is in the form of sugar-coated pills, tablets, syrups or ampoules.

8. The pharmaceutical composition of claim 7, in unitary dosage form.

9. The pharmaceutical composition of claim 5, wherein the excipient is suitable for the parenteral administration of said composition.

10. The pharmaceutical composition of claim 9 wherein the composition is administered in the form of an intramuscular or intravenous injection.

11. The pharmaceutical composition of claim 10 in unitary dosage form.

12. The pharmaceutical composition of claim 5 wherein the excipient is suitable for the rectal administration of the compound.

13. The pharmaceutical composition of claim 12 wherein the composition is in the form of a suppository.

14. The pharmaceutical composition of claim 13 in unitary dosage form.

15. The pharmaceutical composition of claim 5 wherein the excipient is suitable for the topical application of said composition.

16. The pharmaceutical composition of claim 15 wherein the composition is in the form of an ointment or a gel.

17. The pharmaceutical composition of claim 16 in unitary dosage form.

* * * * *